United States Patent [19]

Ducheyne

[11] Patent Number: 4,693,721

[45] Date of Patent: Sep. 15, 1987

[54] POROUS FLEXIBLE METAL FIBER MATERIAL FOR SURGICAL IMPLANTATION

[76] Inventor: Paul Ducheyne, 27 Haymarket La., Bryn Mawr, Pa. 19010

[21] Appl. No.: 854,700

[22] Filed: Apr. 22, 1986

Related U.S. Application Data

[63] Continuation of Ser. No. 661,772, Oct. 17, 1984, abandoned.

[51] Int. Cl.$^4$ .......................... A61F 2/28; A61F 2/02
[52] U.S. Cl. ....................................... 623/16; 623/66; 623/11
[58] Field of Search ...................... 623/16, 22, 23, 66, 623/11

[56] References Cited

U.S. PATENT DOCUMENTS 3,906,550 9/1975 Rostoker et al. ................ 3/1.913 X
4,365,357 12/1982 Draenert .................... 3/1.91

OTHER PUBLICATIONS

Rostoker et al., "Some Mechanical Properties of Sintered Fiber Metal Composites", 1974, pp. 107–112.

*Primary Examiner*—Richard J. Apley
*Assistant Examiner*—Alan W. Cannon
*Attorney, Agent, or Firm*—Sherman and Shalloway

[57] ABSTRACT

Titanium or other biocompatible metal fibers having a diameter of from about 20 to about 200 $\mu$m, a length of from about 2 to 50 mm and a length-to-diameter ratio of at least about 100 are formed into a flexible and deformable mass, for example, a sheet, of interlocked fibers, which may be sintered for additional coherence, to a thickness of from about 0.5 to 30 mm. The amount of fibers is such that the sheet has a voids volume of at least 65%, preferably about 90%. The diameter of the pores of the porous sheet are at least about 150 $\mu$m such that bony tissue can grow in the pores. These porous sheets are highly malleable without loss of structural integrity or pore size distribution. Accordingly, the porous metal fiber mesh sheets are useful for stabilizing prosthetic devices or for general repair of defective bone structures.

8 Claims, 7 Drawing Figures

POROUS FLEXIBLE METAL FIBER MATERIAL FOR SURGICAL IMPLANTATION

This application is a continuation of application Ser. No. 661,772, filed Oct. 17, 1984 abandoned.

FIELD OF THE INVENTION

This invention relates to a new biocompatible porous, flexible metal material for use in bone repair or replacement surgical implantation and procedures which allow bone ingrowth for stabilization of the repaired or replaced bone. More particularly, this invention relates to a flexible porous felt-like metal fiber mesh or pad which can be used to repair or reconstruct defective bones.

DISCUSSION OF THE PRIOR ART

It is known to provide various forms of prosthetic devices such as hip prosthesis with porous surfaces including sintered metal powders to provide a bone ingrowth surface by which the surrounding natural bone can grow into the porous material to help stabilize the implanted device.

For example, Homsey in U.S. Pat. No. 3,992,725 discloses an implantable material having a preferred composition of carbon and graphite fibers, and optionally metallic and ceramic fibers, bonded together by sintered polytetrafluoroethylene (PTFE). These materials are bonded to the surface of an implant to stabilize the implant by fostering ingrowth of bony tissue.

Burstein, et al in U.S. Pat. No. 4,064,567 disclosed a mesh sheath woven of metal wire such as titanium, stainless steel and chrome cobalt. The sheath is used as a reinforcing element with bone cement to arrest crack formation and maintain the shape and integrity of the cement.

In U.S. Pat. No. 3,906,550 to Rostoker and Galante, a porous fiber metal structure is produced by molding and sintering short metal fibers which are preferably kinked prior to being cut into short fibers. In practice the short metal fibers are mechanically molded into the desired precise shapes using constraining dies and moving punches to produce a three-dimensionally mechanically interlocked network of fibers which is then sintered. The sintered fiber metal aggregates have a porosity of 40 to 50% per unit area. The starting metal wires can have diameters ranging from 0.013 cm to 0.030 cm.

A porous metal surface layer is coated by a plasma spraying process on a dense base of the same metal to form a prosthetic device according to the teachings by Hahn in U.S. Pat. No. 3,605,123. The density of the porous surface layer is greatest (substantially pore-free) at the interface with the base and becomes progressively larger towards the exterior surface.

A different approach is provided by Bokros in U.S. Pat. No. 3,048,703. Bokros provides a region of controlled porosity on the exterior surface of a prosthetic device by securing a metal coil spring to the exterior surface.

A structure of varying degrees of porosity from highly dense at the surface of a nonporous plastic stocking to highly porous at the exterior is also provided in European Patent Application No. 0 016 480 published Oct. 1, 1980 in the name of Bernhard Weber. According to this document, a fluid-tight stocking-like liner or inner bag has a textured surface layer obtained by winding filaments of the same material as the liner on the liner while the latter is still on the core on which it is formed. The stocking-like liner bag with textured (porous) surface can be used for anchoring the shaft of an endoprosthesis by means of bone cement placed inside the bag while the surface structure promotes tissue ingrowth.

A stocking-like prosthetic device is also disclosed in German Offenlegungschrift No. 2842847 to Adolph Voorhoeve. According to this device, a funnel-shaped mesh prosthesis can be formed from intersecting and interconnecting steel wires or filaments which permits some deformation in a direction perpendicular to the surface of the mesh and to a lesser degree in the plane of the mesh.

The present inventor has previously provided a porous compound material for prosthetic devices in UK Patent Application GB No. 2 059 267A published Apr. 23, 1981. The compound material includes at least one layer of metal wire mesh joined to a metal substrate by means of metallurgical bonds at the points of contact.

While several of these and other porous materials have been used with varying degrees of success as or in conjunction with prosthetic devices for surgical implantation, there remains a need for porous biocompatible materials which do not require preforming into a specific shape or configuration or bonding to a base metal and which are highly flexible and deformable so as to permit use in a broader variety of applications than previously possible. It would also be desirable to provide a porous bony tissue ingrowth material which can be configured to more closely conform to the bone surface that the material bears against while, at the same time, not being restricted to specific types of surgical procedures such as would be the case for the stocking-like prosthetic devices of the previously mentioned OG No. 2842847 and EPA No. 0 016 480 which are effectively limited to hip-joint endoprosthesis.

One such attempt to provide a flexible porous fiber implantable material suitable for bone ingrowth is described in the above mentioned U.S. Pat. No. 3,992,725 to C. A. Homsy. This patent describes a porous carbon fiber-polytetrafluoroethylene composite sold commercially under the trademark "Proplast." The literature accompanying this product states that the flexible nonmetallic fiber composite has an interconnecting pore size greater than 200 $\mu$m which is a generally acceptable value for bony tissue ingrowth.

However, as reported by Spector, et al "Characteristics of Tissue Growth into Proplast and Porous Polyethylene Implants in Bone" J. of Biomedical Materials Research, Vol. 13, 677–692 (1979), and references cited therein, only fibrous tissue, not bone, forms in the internal pores of Proplast. The authors' analysis showed that Proplast has an average pore size of only 75 $\mu$m and interconnecting pores of less than 50 $\mu$m in diameter. It was concluded that the pore size configuration was an inherent result of the fabrication process in which pores are produced by dissolving salt crystals, which are introduced into the mix of carbon fibers and PTFE, prior to compression, rolling and sintering.

A major problem in total hip prosthesis is the tendency for one or both of the components (femoral component and acetabular component) to become loose. This loosening can result, for example, from bone resorption or degradation of the bone cement. Whatever the cause, when such loosening occurs a marked bone erosion can result and it becomes necessary for the patient to undergo revision surgery. However, revision of a loosened implant is a difficult procedure and present techniques are not entirely satisfactory.

For instance, revision of the femoral component is generally accomplished by one of the following procedures.

A femoral prosthesis similar to the original is reinserted and the cavity is filled up with a thicker cement layer. The problem with this procedure is that it is generally accepted that the cement thickness may not exceed 5 mm at most. With more cement, the maximum temperature during polymerization is conducive to heat necrosis of surrounding bone tissue. Also, a thicker cement is generally considered to be more susceptible to stress cracking failures and to have inferior mechanical properties in general.

As an alternative, a thicker prosthesis has been used with more normal cement thicknesses, e.g. 3 mm. However, by using a thicker metallic stem an unacceptably large proportion of the joint load is carried by the implant rather than by the bone. This is due, in part, to the much higher modulus of elasticity of the metal relative to the bone. A lack of stress in the bone can lead to disuse atrophy. Thus, there will be a high tendency for the newly implanted prosthesis to again loosen due to endosteal resorption.

It has also been proposed to use a wire mesh to reinforce the thicker cement layers to improve their limited strength, however, there are still the problems of high polymerization temperatures and various cytotoxic reactions to the cement.

The funnel-shaped mesh of Voorhoeve (OG No. 2842847) is filled with bone cement and with the prosthetic shaft inserted therein the assembly is inserted in the receiving bone cavity. Although the filamentary form of the mesh permits some deformation, there is still no attempt to have the mesh conform closely to the bone cavity nor is bone ingrowth into the mesh contemplated; rather, the mesh is principally designed to reinforce the cement.

The stocking-like liner of Weber (EPA No. 0 016 480) would appear to offer some improvement in this regard since the liner is sufficiently thin and flexible to permit deformations to conform to the bone cavity when the bag is expanded upon insertion of cement and the prosthetic shaft in the impervious inner bag while the outer textured porous surface permits bone tissue ingrowth. However, while the impervious liner avoids some of the problems caused by the heat of polymerization and the cytotoxicity, there still remains the problem of load distribution between bone, cement and metal prosthesis. In addition, as previously mentioned, these liners are of only limited utility in endoprosthesis.

For the acetabular component, the present procedure is simply to fill up the available spaces by cement. Apart from the previously noted disadvantage of too thick a cement layer, there is also the problem of insufficient bone stock to retain the cemented acetabular cup.

The porous metal fiber structure of Rostoker and Galante (U.S. Pat. No. 3,906,550) can be used to fill the acetabular cavity and be fixed thereto by bony tissue ingrowth. While achieving substantial success, there is still the problem that the material is substantially rigid and not deformable and must be molded precisely to the configuration of the particular cavity and, if necessary, subjected to repressing procedures to achieve a zero clearance fit.

Accordingly, it is an object of this invention to provide a porous deformable and flexible biocompatible material having broad application to reconstructive surgery including repair and/or replacement of defective or damaged bone structure.

It is another object of this invention to provide an improved method of reconstructive bone surgery by providing a flexible bony tissue ingrowth material which can be closely conformed to the surface(s) of the healthy bone being reconstructed, as well as to the geometry of the artificial prosthetic device, in the case of bone replacement surgery, by pressing the flexible material against the surface(s) of the healthy bone being reconstructed.

SUMMARY OF THE INVENTION

These and other objects of the invention which will become apparent from the following more detailed description are generally accomplished by a biocompatible flexible and deformable porous metallic fiber mesh formed by interengaging and intertwining a multiplicity of metallic fibers having a length in the range of from about 2.0 to 50 mm, a diameter in the range of about 20 to about 200 $\mu$m, and thus a length to diameter ratio of at least about 100, the porous fiber mesh sheet having a volumetric porosity of from about 65% to about 95%, and a thickness in the range of from about 0.5 to about 30 mm. The porous mesh material has pore sizes such that bony tissue can penetrate into the pores thereof when the porous mesh is pressed against living bone yet is capable of undergoing substantial bending and shaping without losing its structural integrity, including pore size distribution and volume density. Preferably, the porous mesh is sintered to bond the metal fibers at their cross-over points, i.e. points of contact.

The improved method for replacing a defective portion of a human or animal skeleton with an artificial prosthetic device, such as an artificial hip joint, which has the general configuration of the defective portion which has been surgically removed to form a receiving surface in the remaining portion of the skeleton for mating with the prosthetic device, is accomplished by pressing the above described porous fiber mesh implant material on the receiving surface to thereby conform the mesh to the receiving surface, forming a layer of bone cement on the exposed surface of the mesh and placing the prosthetic device against the layer of bone cement to thereby force the cement into the pores in the exposed surface, the cement penetrating only through a portion of the total thickness of the fiber mesh implant, whereby setting of the bone cement provides immediate stabilization of the prosthetic device. Long term stabilization is provided by ingrowth of bony tissue into the pores of the mesh which are in contact with the receiving surface of the healthy bone.

In repairing or reconstructing a defective bone structure including one or more cracks or voids or other openings or spaces, the cracks or voids are simply filled with the above described flexible porous metal fiber mesh implant material with or without addition of bone cement, such that the porous fiber mesh closely conforms to the surfaces of the healthy bone in the vicinity of the cracks or voids whereby bony tissue can grow into the pores of the porous mesh.

BRIEF DESCRIPTION OF THE DRAWINGS

The invention will now be described in greater detail with reference to specific embodiments thereof and with the aid of the accompanying drawings in which.

DETAILED DESCRIPTION OF THE INVENTION

Figure 1:
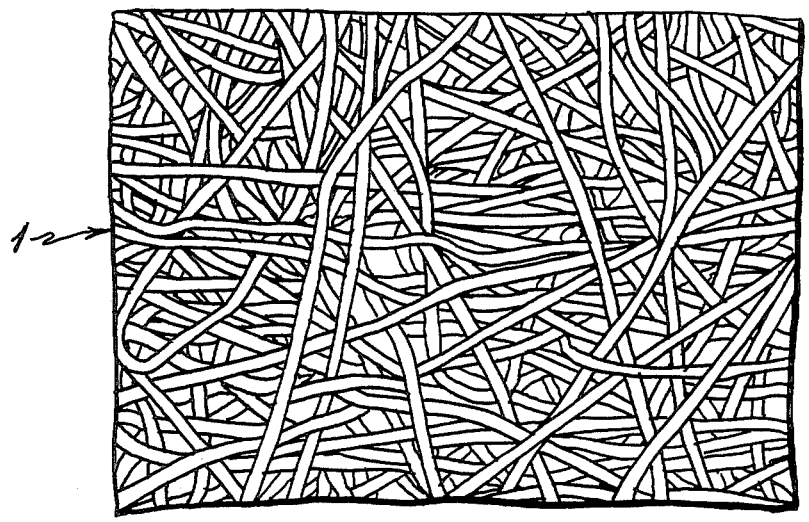
FIG. 1 is a scanning electron microscopic image (magnification 50×) of porous fiber mesh according to the invention.

Any material for surgical implantation must necessarily meet certain criteria. Several of these are mentioned in the aforementioned U.S. Pat. No. 3,992,725, and include bio-compatibility, resistance to chemical migration when implanted, stability for autoclaving, and porosity for tissue ingrowth, and resiliency. In addition, a satisfactory porous material for implantation should naturally have sufficient strength characteristics to withstand and accomodate a wide range of stresses and, in particular, the strength of the porous implant material, as well as the bonding between the porous implant material and the bulk implant, must exceed the stress levels that are expected to be encountered in vivo. It is also preferred that the implanted porous insert should possess elastic properties approaching those of the surrounding tissues in order to minimize the stress peaks at the interface between the porous material and the insert.

The porous implant material according to the invention satisfies all of the foregoing requirements. Bicompatibility and resistance to chemical migration and stability for autoclaving are all provided by selection of appropriate metals for the metallic fibers. Many such metals have been known for use in surgical devices, for example, cobalt-chromium alloys, titanium, tantalum, niobium, alloys of these metals, and the like. Titanium is the preferred metal since its biocompatibility is well documented and in addition its low modulus of elasticity increases the overall flexibility of the porous sheets produced from the titanium fibers. Other metal fibers, such as stainless steel fibers, may also be used for certain applications but because of the possibility of crevice corrosion inside the interstices of the porous material the use of stainless steel fibers is not generally recommended.

Since the porous metal fiber mesh implant material is produced without addition of chemical binders or other fibers and since these biocompatible materials are highly inert to body fluids, there is substantially no likelihood of chemical migration of the implanted porous material.

In addition to possessing the foregoing properties, the porous metal fiber mesh material is resilient, i.e. flexible, and it is also highly deformable by simple hand or tool manipulation. That is, the porous mesh of this invention is capable of being deformed without loss of structural integrity and without diminution of pore volume or pore size as is apparently the case with the porous materials of the aforementioned U.S. Pat. No. 3,992,725. Still further, the porous mesh of this invention can be easily deformed to the desired configuration at the time of surgery using available instruments and acceptable operating room procedures. Therefore, unlike prior porous insert materials, it is not necessary to preform the porous mesh by complicated molding or other shaping procedures and it is also not necessary to bond the shaped porous mesh to the orthopedic or prosthetic appliance or wear surface.

According to this invention, the critically important characteristics of pore size and deformability are achieved by careful control and selection of the following three parameters of the porous metal fiber mesh:

1. fiber diameter and fiber length;
2. thickness of the porous mesh sheet; and
3. porosity or volumetric density of the porous mesh sheet.

In general, the deformability, or malleability, of the porous mesh sheet can be improved by decreasing the volumetric density (i.e. increasing porosity) and by decreasing the thickness of the porous mesh. However, the volumetric density and thickness parameters cannot be decreased in an unlimited way since other characteristics of the porous mesh are also affected by these parameters. Therefore, it is necessary to limit the above parameters to within well defined and critical limits.

1. Fiber diameter and length; as the fiber diameter is decreased, the mesh sheet becomes more flexible and deformable, but the pore size also becomes smaller. The fiber length must be controlled to provide a balance between coherency and flexibility.

The fiber length should be within the range of from about 2 mm to about 50 mm, preferably about from 2.5 to about 30 mm and more preferably from about 8 mm to about 25 mm. The fiber diameter should be within the range of from about 20 microns to about 200 $\mu$m, preferably from about 20 $\mu$m to about 150 $\mu$m, and more preferably from about 40 $\mu$m to about 100 $\mu$m. If the fiber length is less than about 2 millimeters, it is difficult to produce a coherent mass of fibers. If the fiber length is more than about 50 mm, the manufacturing becomes difficult. In particular, for fiber lengths in excess of about 50 mm, sieving the fibers becomes impractical if not impossible. If the diameter of the fibers is less than about 20 microns, it is difficult to maintain the average pore size of at least 150 $\mu$m needed to assure ingrowth of bony tissue. If the fiber diameter is greater than about 200 $\mu$m, the flexibility and deformability become insufficient.

Within these ranges of fiber length and diameter, it is preferred that the fiber length-to-diameter ratio be at least about 100, preferably at least about 125 and more preferably at least 200. Thus, for a given diameter fiber, the fiber length should be selected to give an L/D ratio which will ensure a coherent mass of fibers.

2. Thickness: as the thickness of the porous fiber mesh decreases, the fiber mesh material becomes more flexible, but below about 0.5 millimeters, the coherency of the fiber mesh becomes unsatisfactory with thick fibers. At a thickness above about 30 mm, the porous mesh cannot be readily deformed. Accordingly, the thickness of the porous mesh should be within the range of from about 0.5 mm to about 30 mm, preferably from about 1 mm to about 15 mm.

3. Porosity: as the porosity increases (volumetric density decreases) both flexibility/deformability and pore size increase, but the coherency of the fiber mesh decreases.

The porous metal fiber mesh implant material according to this invention has an usually high porosity of at least about 65%, preferably from about 70% to about 95%, especially preferably from about 80% to about 92%. As used herein, and in the appended claims, "porosity" refers to the voids or pore volume of the porous fiber mesh and is the converse of the "volumetric density" which is the amount, by volume, of fibers per unit volume of the porous fiber mesh sheet. Thus "porosity" (%)=100% - "volumetric density" (%). Furthermore, the porosity or volumetric density may vary slightly from region to region of the porous metal fiber mesh and it is sufficient if the average value of porosity or volumetric density over the entire cross-section of the porous fiber mesh falls within the foregoing values.

Similarly, it is possible for a small amount, for example, less than about 20% by weight, preferably less than about 10% by weight, especially preferably less than about 5% by weight, of the total fibers to have diameters and/or lengths and/or length-to-diameter ratios outside of the values specified above, so long as the average values fall within the prescribed limits.

In order to improve the coherency of the porous metal fiber mesh and to prevent or at least minimize the displacement of individual fibers within the mesh, or even the complete removal of individual fibers from the mesh, it is preferred to subject the porous mesh to a heat treatment sufficient to sinter the individual metal fibers to each other. The sintering operation is a solid state diffusion process by which metal to metal bonds are formed between individual fibers. While the sintering operation results in some reduction in flexibility and deformability by virtue of the metal to metal bonds which restrains the relative displacement of the fibers this reduction is offset by the reduction in loss of fibers during handling and implantation.

The porous metal fiber mesh implant material can be fabricated by usual techniques including sieving the fibers to the appropriate size range, compacting the fibers into a sheet-like structure or other desired form, and preferably sintering. In the compacting step, the amount of fibers needed is calculated based on the average fiber size and the desired thickness and porosity (or volumetric density) the amount of fibers needed to fill the available space can be readily calculated or determined by routine experimentation.

After the metal fibers are sieved, they can be directly laid down on a suitable surface, e.g. a mold to form a loosely packaged mass of interlocked metal fibers, or they may be mixed with a suitable liquid to form a slurry of the fibers. In the latter case, the slurry is then filtered through appropriately sized filter paper to form a loosely packed sheet of interlocked metal fibers. The loosely packed mass, after removal of the remaining liquid, if present, is compressed between flat surfaces, one or both of which may be heated to remove any residual liquid until the predetermined thickness is reached. The amount of pressure to be applied will depend on various factors such as the type of fiber, thickness and porosity, but generally pressures in the range of from about 4 to about 200 MPa are satisfactory. Alternatively, the sieved fibers may be picked up and laid down from an air slurry according to known techniques.

In forming the fiber slurry, filtering the slurry, compacting, sintering and any other steps in handling or treating the metallic fibers some degree of care should be taken to avoid substantial bending or twisting of the fibers out of their informal linear configuration since the flexibility and deformability of the resulting product will decrease as the fibers become more nonlinear, presumably as a result of the greater number of contact points between fibers per unit area.

For example, a sheet of the porous metal fiber mesh having a thickness of about 3 mm and an average density of about 10 to 15% can be prepared from commercial purity titanium fibers having an average diameter of about 50 $\mu$m and an average length of about 20 mm by first sieving the fibers to deglomerate any clumps or masses. The sieved fibers are directly fed into an appropriately sized vessel, for example, measuring 15 cm $\times$ 15 cm, while exercising care to obtain a uniform distribution of the fibers and avoid reagglomeration. A sufficient amount of fibers are deposited to obtain a thickness of from about 4 to 5 cm. This loose mass of fibers is transferred to a hydraulic press having two platens, each measuring 12$\times$6 cm, and the mass is subjected to a pressure of about 6 to 10 MPa, preferably about 8 MPa, for about 1 to 10 seconds, preferably 2 to 4 seconds. The edges of the resulting sheet are cut off by the press to obtain 2 sheets, each measuring 120$\times$60$\times$3 mm.

Preferably, the porous metal fiber sheets are then sintered to improve the cohesion by forming metal to metal bonds at the fiber cross-over points. Sintering can be carried out, for example, by placing the fiber sheets, laid between $Al_2O_3$ plates of about 300 g each, in a vacuum furnace (e.g. at $10^{-4}$ torr or lower), which is heated to about 900° C. for about 30 minutes.

By using metal fibers within the size limitations described above and controling the amount of fibers in the porous mesh to provide the thicknesses and porosities described above, the porous mesh will have a pore size distribution such that at least 50 percent, preferably at least 80 percent, especially preferably about 100% of the pores will have a pore size of at least 150 $\mu$m, preferably from about 150 $\mu$m to about 600 $\mu$m. As used herein "pore size distribution" refers both to the pores at the surface of the fiber sheet and throughout the thickness of the fiber sheet.

Figure 2:
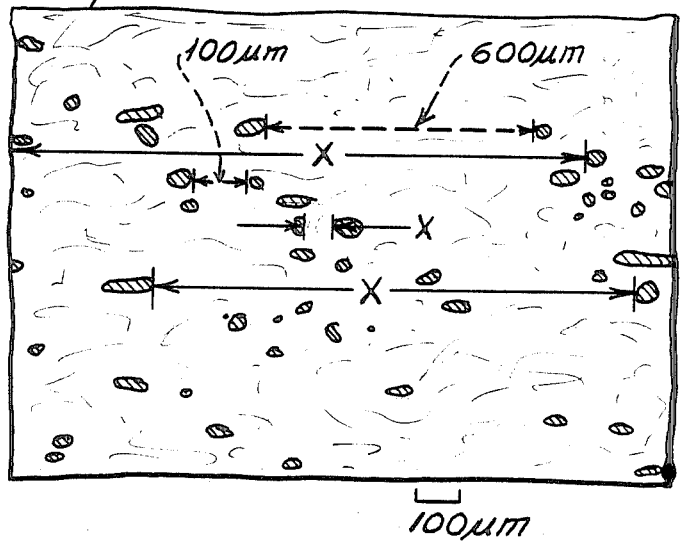
FIG. 2 is a cross-sectional micrograph of the porous fiber mesh shown in FIG. 1.

For a porous fiber material with an average porosity of as high 65 to 95%, it is difficult to exactly define what the pore size is. To appreciate the difficulty, it may be helpful to consider both a scanning electron microscopic image (FIG. 1) and a cross-sectional micrograph of a typical porous material with a 90% porosity (FIG. 2). The cross-sectional micrograph shows the abundance of porosity. It would be logical to determine a pore dimension parallel with the surface of the sheet since the efficacy of either bone cement intrusion or bony ingrowth would primarily depend upon the pore dimension perpendicular to the intrusion or ingrowth direction. A widely used method to measure such dimensions is a stereometrical method: the line intercepts of pores are measured on micrographs on a set of lines that are projected on the micrograph, independently from the analyst. However, with the present porous material this is bound to yield data without physical meaning; for example, on FIG. 2 various possible intercepts without meaning are indicated by an "X." That is, these pores are not accessible over their entire length, i.e. are blocked by other fibers, for bony ingrowth or cement intrusion.

From these considerations, it appears appropriate to indicate an estimate for the range of available pore sizes. This can be obtained from the scanning micrograph: the fibers in FIG. 1 have a diameter of 50 μm. Interstices range from about 100 to 600 μm and predominantly from about 150 to 600 μm In addition to the pore size distribution being sufficient to permit ingrowth of bony tissue, the fiber mesh implant material has a porosity and pore size distribution which permits bone cement to penetrate through the interstices of the mesh using slight thumb pressure. For example, the bone cements contemplated include substantially all types of bone cements now used in surgical procedures. The most common of these are bone cements based on polymethyl methacrylate, generally a combination of polymer powder and liquid monomer which polymerizes in situ. Bone cements may be of the high viscosity type, i.e. viscosities ranging from about 1000 to about 4000 cps, or low viscosity type, viscosities ranging from about 10 to about 1000 cps. The bone cements preferably have a viscosity such that during surgery the cement will penetrate through only a portion of the thickness of a porous metal fiber mesh sheet, generally from about 1/10 to about ½, preferably from about ¼ to about ½ of the thickness of a fiber sheet so that sufficient volume remains in the bone facing side of the sheet to permit bony tissue ingrowth. Polymethylmethacrylate bone cements having viscosities (before setting) in the range of from about 1000 to about 4000 cps are preferred, such as, for example, Zimmer ® Bone Cement, Catalogue N. 1102-02, (40 grams polymer powder and 20 grams monomer liquid).

Figure 4:
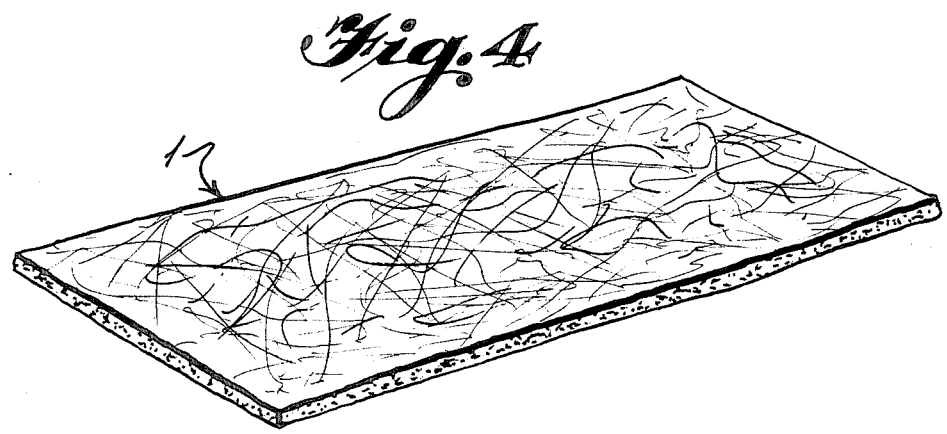
FIG. 4 is a perspective view of a typical specimen, in sheet form, of the porous fiber mesh implant material.

Preferably, the porous metal fiber mesh implant material 1 is provided in sheet form, such as shown in FIG. 4. A typical large sheet may, for example, have the dimensions of 60×120×3 mm, and can be cut into smaller sizes, or folded upon itself into two or more layers, as necessary. It is also possible, due to the flexibility of the porous fiber mesh material, to form continuous length sheets which can be stored in rolled up form and dispensed in suitable lengths, as needed.

For some applications, such as mandibular reconstruction, or acetabular prostheses, for example, the porous fiber mesh implant material can be provided in the form of a coherent mass which may be configured into the desired shape, or the mass may be pressed to the general configuration desired, and supplemented, if necessary, with addition of porous fiber implant material.

The flexible porous metal fiber mesh has a broad range of applications in bone surgery for example, mandibular reconstruction including fixation of artificial teeth, revision surgery of the hip joint and other joint prostheses and implant procedures, and generally for any procedure where a normal regrowth of bone tissue cannot be expected.

In the case of mandibular reconstruction a cavity is prepared in the jawbone and the cavity is manually filled with a mass of the porous ingrowth material in an amount sufficient to augment or reconstruct the mandibular. Where there is insufficient bone to form a cavity it may be necessary to provide means for initial stability. The stabilization means can take the form of suture wires or bone cement, for example. The flexibility and deformability of the porous material permits the metal fiber mass to be closely conformed or adapted to the existing bone surfaces, as well as to the desired final configuration for reconstruction. It is a distinct advantage of the porous material of this invention that the precise shaping can be easily accomplished during the surgical procedure without destruction of the pores size distribution required for bony tissue ingrowth.

Figure 5:
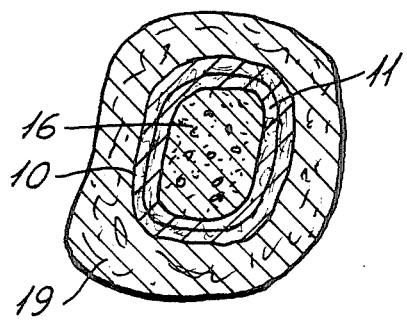
FIG. 5 is a schematic cross-sectional view of the fiber mesh implanted in the femoral canal with cement.
Figure 6:
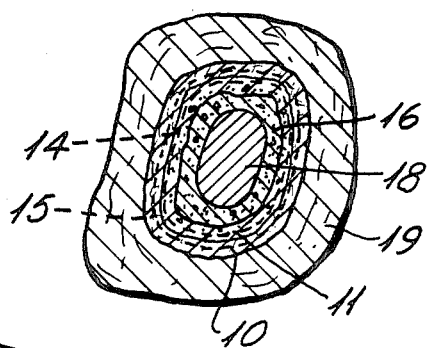
FIG. 6 is a schematic cross-sectional view of the fiber mesh implant material used with a hip prosthesis.

For revision surgery of the femoral component, a hip prosthesis with a normal stem thickness can be used by pressing one or more layers of porous fiber sheet material in the previously prepared femoral canal against the bone while leaving a central opening to receive the hip stem with sufficient room to surround the stem with a thickness of bone cement of from about 1 mm to about 4 mm. As seen in FIG. 5, two layers 10 and 11 of the porous metal fiber sheets, each having a thickness of 4 mm, are pressed against and conformed to the cortical bone 19. The resulting cavity is filled with bone cement 16 and the hip stem 18 (FIG. 6) is then fitted centrally within the cavity thereby causing a portion of the cement to penetrate into the inner layer 11 of the porous sheet material as shown at 14. The thickness of the bone cement between the inner layer 11 and the surface of the stem 18 ranges from 1 to 4 mm depending on the diameter of the femoral canal. If necessary, to accommodate the tapering diameter of the femoral canal, it may be sufficient to use fewer layers of the porous material at the bottom end of the femoral canal than at the higher and wider end of the femoral canal.

Accordingly, it is possible to use both a normal thickness of bone cement and a normal thickness of the metal hip stem. In view of the ability to shape the porous insert material, it can be closely contacted with the bone without closing the pores of the insert material. Thus, long term stabilization of the hip prosthesis is accomplished as the cortical bone grows into the pores of layer 10 as shown at 15 while immediate stabilization between the stem and insert material is provided upon setting of the bone cement against the stem and in the pores of layer 11.

A still further advantage of the insert material of this invention is that its modulus of elasticity closely approximates that of the bone. This substantially eliminates the risk of having greatly altered stress levels in the cortex.

The mechanical and elastic properties of a typical porous insert material of the invention made from titanium fibers of 50 μm diameter and 20 mm length at a density of about 10% (90% pore volume) at a sheet thickness of 3.5 mm, sintered at 900° C. for 30 minutes is determined as follows:

A specimen measuring 14 mm×120 mm is supported from below at two points 90 mm apart, 15 mm in from each end. Two load points are spaced 50 mm apart, 35 mm in from each end. Measurements of load displacement are made with an Instron TT-DM-L testing machine at a cross head speed of 5 mm/min.

Figure 3:
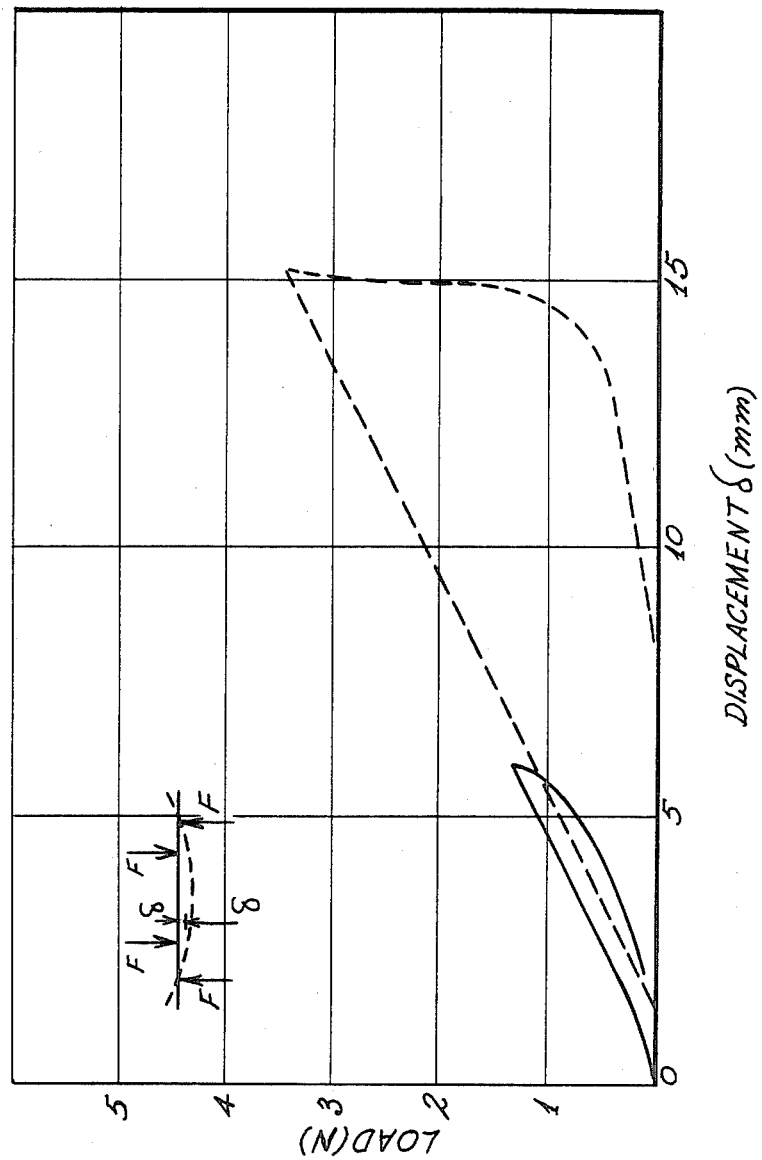
FIG. 3 is a typical load displacement curve for a porous fiber mesh according to the invention.

A typical load displacement curve is shown in FIG. 3. It shows two loading-unloading cycles; the first one is shown in full line, the second one is shown as a dotted line. After unloading, there is a permanent deformation as shown in FIG. 3. This permanent or residual deformation ($\delta_r$) is at the most only half of the maximum or total deformation ($\delta_t$). This clearly shows the excellent deformability of the material. The second loading cycle of FIG. 3 is characterized by a maximum force F of 3.65 N. The maximum stress in the porous sheet at that moment is 2.8 MPa and the total deformation $\delta_t = 13.8$ mm. Upon unloading the residual deformation is $\delta_r = 6.3$ mm.

The apparent modulus of elasticity can be defined from the plot as the slope of the loading portion of the graph. The modulus thus defined represents the apparent elasticity of the porous sheet in the plane of the sheet. Values between 80 and 100 MPa were measured;

the variation may be accounted for by slight variations in density. These data substantiate the fact that the elasticity of the porous fiber implant is close to the elastic properties of trabecular bone into which it is implanted.

Figure 7:
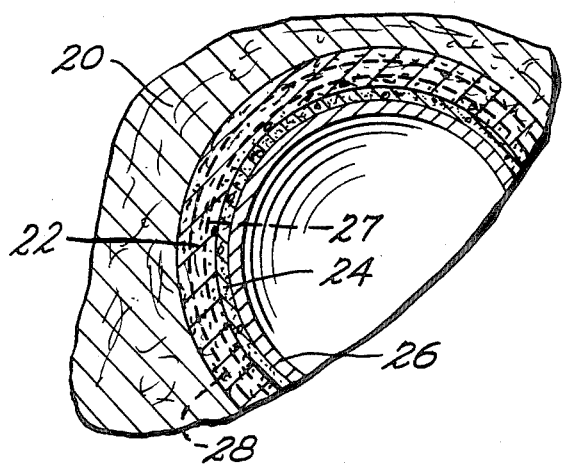
FIG. 7 is a schematic cross-sectional view of the fiber mesh implant material used with an acetabular prosthesis.

For an acetabular prostheses, as shown in FIG. 7, the acetabular floor 20 is covered with at least one layer 22 of the porous insert material. A layer of polymethyl methacrylate bone cement 24 is provided on the porous insert layer and the acetabular prosthesis, for example, a high density polyethylene cup prosthesis 26, is placed on the cement with sufficient pressure to force the viscous bone cement into at least the pores on the surface of the porous fiber insert material, as shown at 27, to provide initial stabilization. Long term stabilization is provided as bony tissue grows into the pores of the insert, for example, to a depth shown by dotted line 28, which has been placed in close contact and conformity with the bone stock of the acetabular floor.

For general bone repair the porous material can used as a bone filling material by packing it into a defect or void in the bone. If desired, after positioning of the porous insert material a bone cement can be injected to penetrate throughout the interstices of the porous insert. The volume of cement can be determined to fill up all or only a portion of the available volume. This can result in a composite reinforced cement of improved toughness and strength while still allowing bone tissue ingrowth.

What is claimed is:

1. A biocompatible flexible and deformable porous metallic fiber mesh sheet which is useful in reconstructive surgery, said sheet consisting essentially of a multiplicity of interengaged and intertwined biologically inert metallic fibers, each of said fibers having a length in the range of about 2 to about 50 millimeters, and a diameter in the range of about 20 to about 200 micrometers; said fibers being interengaged and intertwined with each other to form a porous mesh having a porosity of at least about 80% and a thickness in the range of from about 0.5 to about 30 millimeters, said mesh sheet being flexible by simple hand or surgical tool manipulation and permanently deformably without losing its structural integrity and being characterized by a porosity such that bony tissue can penetrate into the pores of said mesh when said mesh is pressed against the surface of the skeletal structure of a living human or animal.

2. A porous fiber mesh sheet according to claim 1 wherein said metallic fibers are sintered at their points of contact.

3. A porous fiber mesh sheet according to claim 2 wherein said biocompatible metal fibers are selected from the group consisting of cobalt-chromium alloy, titanium, titanium alloy, tantalum, tantalum alloy, stainless steel, niobium and niobium alloy.

4. A porous fiber mesh sheet according to claim 3 wherein said metallic fibers are titanium metal fibers.

5. A porous fiber mesh sheet according to claim 1 which has a porosity such that at least 50 percent of the pores of the mesh have a pore size of at least about 150 micrometers.

6. A porous fiber mesh sheet according to claim 1 wherein said fibers have a length in the range of from about 8 to about 25 millimeters, a diameter in the range of from about 40 to about 100 micrometers and a length-to-diameter ratio of at least about 125; said porous mesh having a porosity of between about 80% and about 95% and a thickness in the range of from about 1 to about 15 millimeters.

7. A biocompatible flexible and permanently deformable porous metallic fiber mesh sheet consisting essentially of a multiplicity of interengaged and intertwined biologically inert metallic fibers, each of said fibers having a length in the range of about 2 to about 50 millimeters, and a diameter in the range of from about 40 to about 100 micrometers; said fibers being interengaged and intertwined with each other to form a porous mesh having a porosity of from about 80% to about 95%, and a thickness in the range of from about 0.5 to 30 millimeters, said mesh sheet being flexible and permanently deformable without losing its structural integrity and being characterized by an elasticity approximately the same as the elastic properties of trabecular bone, and being further characterized by having an apparent modulus of elasticity in the range of from about 80 to about 100 MPa and by a porosity such that bony tissue can penetrate into the pores of said mesh when said mesh is pressed against the surface of the skeletal structure of a living human or animal.

8. A biocompatible flexible and permanently deformable porous metallic fiber mesh sheet consisting essentially of a multiplicity of interengaged and intertwined biologically inert substantially straight metallic fibers, each of said fibers having a length in the range of about 2 to about 50 millimeters, and a diameter in the range of from about 40 to about 100 micrometers; said fibers being interengaged and intertwined with each other to form a porous mesh having a porosity of from about 80% to about 95%, and a thickness in the range of from about 0.5 to about 30 millimeters, said mesh sheet being flexible and permanently deformable without losing its structural integrity and being characterized by an elasticity approximately the same as the elastic properties of trabecular bone, and being further characterized by a porosity such that bony tissue can penetrate into the pores of said mesh when said mesh is pressed against the surface of the skeletal structure of a living human or animal.

* * * * *